United States Patent
Effenhauser et al.

(10) Patent No.: US 7,118,351 B2
(45) Date of Patent: Oct. 10, 2006

(54) MICROPUMP WITH HEATING ELEMENTS FOR A PULSED OPERATION

(75) Inventors: Carlo Effenhauser, Weinheim (DE); Herbert Harttig, Altrip (DE); Tony Ziegler, Steinfeld (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 361 days.

(21) Appl. No.: 10/436,387

(22) Filed: May 12, 2003

(65) Prior Publication Data
US 2003/0215334 A1 Nov. 20, 2003

(30) Foreign Application Priority Data
May 16, 2002 (DE) .................. 102 22 228

(51) Int. Cl.
*F04B 19/24* (2006.01)
(52) U.S. Cl. ............................................... 417/208
(58) Field of Classification Search ................ 417/208
See application file for complete search history.

(56) References Cited

U.S. PATENT DOCUMENTS

| | | |
|---|---|---|
| 4,790,640 A | 12/1988 | Nason |
| 4,792,283 A | 12/1988 | Okayasu |
| 5,129,788 A | 7/1992 | Okayasu |
| 5,171,132 A | 12/1992 | Miyazaki et al. |
| 5,249,929 A | 10/1993 | Miller, Jr. et al. |
| 5,336,062 A | 8/1994 | Richter |
| 5,370,842 A | 12/1994 | Miyazaki et al. |
| 5,375,979 A | 12/1994 | Trah |
| 5,495,105 A | 2/1996 | Nishimura et al. |
| 5,599,502 A | 2/1997 | Miyazaki et al. |
| 5,969,739 A | 10/1999 | Altendorf et al. |
| 6,071,081 A | 6/2000 | Shiraishi |
| 6,162,046 A * | 12/2000 | Young et al. ............... 431/11 |
| 6,634,864 B1 * | 10/2003 | Young et al. ............... 417/208 |
| 2005/0006309 A1 | 1/2005 | Effenhauser et al. |

FOREIGN PATENT DOCUMENTS

| | | |
|---|---|---|
| DE | 149785 | 9/1931 |
| DE | 19860227 C1 | 5/2000 |
| EP | 0 268 237 B1 | 5/1988 |
| EP | 0 421 406 A2 | 4/1991 |
| EP | 0 421 406 B1 | 4/1991 |
| EP | 0 545 284 A1 | 6/1993 |
| EP | 0 545 284 B1 | 6/1993 |
| EP | 0 556 748 A2 | 8/1993 |
| EP | 0 556 748 A3 | 8/1993 |
| EP | 0 556 748 B1 | 8/1993 |
| EP | 0 568 024 A2 | 11/1993 |
| EP | 0 568 024 A3 | 11/1993 |
| EP | 1167757 A2 | 1/2002 |
| JP | 04-126995 | 4/1992 |
| JP | 11-108572 | 4/1999 |
| JP | 2000-040488 | 2/2000 |

(Continued)

*Primary Examiner*—Charles G. Freay
(74) *Attorney, Agent, or Firm*—Woodard, Emhardt, Moriarty, McNett & Henry LLP (57) ABSTRACT

The invention discloses a micropump having heating elements in which an essentially pulsed operation of the heating elements occurs by means of a control unit. The pulsed operation of the heating elements enables an exact control of the flow rate. With the aid of the control unit it is possible to keep the flow rate constant over a long period of days or to change the flow rate rapidly and precisely.

19 Claims, 4 Drawing Sheets

FOREIGN PATENT DOCUMENTS

| | | |
|---|---|---|
| WO | WO 97/40939 | 11/1997 |
| WO | WO 99/39120 | 8/1999 |
| WO | WO 99/39005 | 9/1999 |
| WO | WO 00/25921 | 5/2000 |
| WO | WO 00/63668 | 10/2000 |

* cited by examiner

MICROPUMP WITH HEATING ELEMENTS FOR A PULSED OPERATION

RELATED APPLICATION DATA

The present application is based upon and claims priority to German Patent Application Serial No. 102 22 228.2 filed May 16, 2002, the disclosure of which is incorporated by reference.

The present invention concerns a micropump and the control of a micropump for low flow rates in particular in the range of 1 to 1000 nl/min. The pump according to the invention operates a heating element discontinuously and produces constant flow rates despite a pulsed type of operation. The micropump can be used to maintain liquid transport over a period of several days at a constant flow rate, and if necessary the flow rate can be quickly changed and precisely reset.

The invention also encompasses a microdialysis and ultrafiltration system comprising an above-mentioned pump and a method for operating the pump.

Microdialysis and ultrafiltration are mentioned in the following as examples of possible applications of the micropump according to the invention. The micropump has proven to be of particular advantage for applications in the overall field of medical diagnostics.

The principle of microdialysis is illustrated in the following on the basis of the disease diabetes where it represents a promising approach for continuous glucose monitoring.

At present over 140 million people suffer worldwide from diabetes. It is estimated that the number of diabetics will increase in the next 25 years to ca. 300 million. Inadequate measures to control the blood glucose level can over many years lead to long-term complications in diabetics. This may for example lead to retinopathy which causes loss of sight, or renal or nervous diseases or diseases of the coronary vessels. Another risk is the so-called hypoglycaemic shock state when the blood sugar concentration is too low which can lead to death, especially at night. At present blood sugar is monitored using lancing aids and test strips. They have the major disadvantage that large variations in the blood sugar level (e.g. food intake) may be overlooked since the glucose values are not measured often enough (ca. 1–4 measurements per day). For these reasons a continuous monitoring of the blood sugar level is desirable for high-risk patients (e.g. for insulin-dependent diabetics). In this connection it is particularly important that critical conditions are rapidly detected so that countermeasures can be implemented.

A very promising approach for continuous glucose monitoring is based on the principle of microdialysis. In this process glucose from the interstitial fluid diffuses through a dialysis membrane into a dialysis solution. A catheter containing the membrane is inserted into the subcutaneous fat tissue of the patient. An electrochemical glucose sensor is located downstream of the catheter. Provided the dialysis solution remains for an adequately long time within the exchange area of the membrane, the glucose concentration in the dialysis solution adapts very well to the glucose concentration in the interstitial fluid so that the glucose concentration can be accurately determined. Such a catheter is usually used for several days and hence important requirements for a micropump can be defined in this example of a field of application. Some of these requirements are for example a constant flow rate over a period of several days, a precise and direct control of the micropump, a low energy consumption, low manufacturing costs when using the micropump as a disposable product and sterilizability.

Miniaturized pumps are known in the prior art e.g. squeezed tube pumps which can be used to achieve flow rates of down to about 100 nl/min depending on the tube diameters that are used. In the prior art the main development goal of miniaturized pumps has usually been to achieve the highest possible delivery rate with a minimal pump volume. However, it has turned out that when used over long periods such pumps do not work reliably in the lower output range, it is difficult to avoid large variations in the flow rates and in particular their low-cost manufacture as a disposable product represents an enormous hurdle.

Other devices are known in the field of microdialysis and ultrafiltration in which a negative pressure reservoir (for example a drawn syringe) is connected via a constricted capillary path with a fluid system. However, this has the drawback that the pressure time course is not linear which can only be improved by a negative pressure reservoir of a larger volume which is also disadvantageous.

Another device for achieving low flow rates is known from the document EP-B 0 722 288. In this device a liquid in a channel is directly contacted with a sorbent material. Such a system typically has flow rates in the range of a few microlitres per minute.

The document EP 0 568 024 discloses a pump in which heating elements are positioned outside a capillary. When the heating elements are activated, liquid is evaporated at the end of the capillary resulting in a pumping effect.

However, a disadvantage of this pump is that the end of the capillary is heated by the heating process and a constant flow rate can only be ensured by a complicated temperature control mechanism. A change in the flow rate also requires a temperature control mechanism which varies the flow rate by changing the temperature of the heating elements. In addition it has turned out that the relationship between temperature and flow rate is unlinear and depends on the material. The thermal conductivity and heat capacity of the liquid and capillary are important factors that influence the temperature dependency of the flow rate and make a precise control more difficult. Hence such temperature control mechanisms only allow a slow change in the flow rate due to the sluggishness of the control mechanism.

Although several types of micropumps already exist, the pumps known in the prior art often only inadequately fulfil the said requirements. In particular it has often proven to be difficult to achieve a simple to handle, low-cost and exact control of micropumps.

The object of the present invention is to provide a micropump and a method for operating the micropump which fulfils the said requirements and in particular should enable the flow rate to be controlled in a simple manner.

The micropump according to the invention with a heating element comprises a fluidic transport element that can be connected with a liquid reservoir and in the connected state makes a fluid connection between the fluid reservoir and an evaporation area. The heating element is positioned in the area of one end of the fluidic transport element. The pump also comprises a control unit for controlling the heating element. As a result of signals sent to the heating element by the control unit, the heating element is alternately in a resting phase for a time period T1 and in a heating phase for a time period T2. The resting and heating phase alternate periodically resulting in a pulsed operation of the heating element.

Furthermore a micropump having the said properties is a subject matter of the invention in which the fluidic transport element is connected with a liquid reservoir and the transport element is filled with liquid.

When the pump according to the invention is delivered there is preferably no direct contact of liquid with the end of the transport element to avoid an unnecessary consumption of liquid due to evaporation of liquid at ambient temperature. The liquid can be contacted with the end of the transport element by the operator for example by a specific pressure impulse when the pump is put into operation. Liquid can now be evaporated in a metered manner by specifically heating the end of the transport element.

The micropump according to the invention is characterized by constant flow rates of high reproducibility that can be rapidly set and adjusted.

The micropump is also characterized in that it is simple and cost-effective to manufacture and is preferably compatible with the manufacture of microfluidic systems based on planar technology (e.g. microtechnology).

Another characteristic feature of the micropump is that it is compatible with several sterilization processes e.g. $\beta$, $\gamma$, steam and ETD gas sterilization.

Liquid is removed from the transport element by the evaporation process resulting in a desired pumping effect by the subsequent inflow of liquid.

The term evaporation in the sense of the invention means an evaporation of liquid below its boiling point and also an evaporation of liquid above its boiling point.

The pump can for example be used to transport a liquid which is used as a perfusion liquid for microdialysis. In this case the perfusion liquid flows through the microdialysis system during which an analyte to be determined is taken up in the perfusion liquid and measured downstream of the microdialysis membrane. When the pump is used in the field of ultrafiltration, the evaporation of a liquid generates a negative pressure in the fluidic transport element which transports another fluid from the environment into the fluidic transport element. In the case of ultrafiltration this other fluid is interstitial fluid from the body of a patient which enters the channel through an ultrafiltration membrane. For example the liquid to be evaporated is fluidically coupled to the interstitial fluid resulting in a transport of the interstitial fluid. The fluids are then segmented from one another in the fluid channel. The fluid coupling can for example be accomplished by means of an air bubble or a liquid that is immiscible with the two liquids as described for example in EP 1 167 757.

Any liquids can be used within the scope of the invention but aqueous liquids are preferably used. In addition to the aqueous component, the aqueous liquids can contain substances or mixtures of substances which influence the surface tension and/or viscosity which in turn have an effect on the flow rate of the liquid in the fluidic transport element. The liquids preferably have no substances or only small amounts of substances such as salts that cannot evaporate in the temperature range in which the pump operates since they would accumulate at the end of the transport element as a result of the evaporation process and could lead to a blockage of the fluidic transport element. Hence only completely evaporable components e.g. alcohols are advantageously used as liquids.

In the pump according to the invention the heating element is located in an area at the end of the fluidic transport element and this end is designed such that evaporated liquid can escape from the end of the transport element. According to the invention the area at the end of the fluidic transport element is delimited to the extent that the heating element can only extend into the interior of the fluidic transport element to such an extent that during heating and evaporation of liquid essentially no bubbles are formed in the transport element that could lead to unevaporated liquid being ejected from the transport element. This ensures that only evaporated liquid escapes from the transport element.

The micropump according to the invention is characterized in that a pulsed operation of a heating element causes a metered evaporation of liquid resulting in a sufficiently continuous pumping effect for the application and thus enabling a simple and exact control of the flow rate. The principle is briefly elucidated in the following.

Initially the heating element is in a resting phase T1 in which the fluidic transport element is essentially completely filled with the liquid to be transported. The heating element is activated for a time period T2 such that the end of the transport element is heated in the heating phase. The released heat evaporates liquid in the area of the end of the transport element. The amount of liquid evaporated during T2 depends on the degree of filling of the end of the capillary with the heating element, on the duration of the heating phase T2, on the amount of delivered heat and on the partial vapour pressure of the liquid in the atmosphere. During the heating phase T2, individual discrete portions of liquid are transformed into the gas phase by evaporation. The mean amount of heat released can be exactly dosed by changing the parameters T1, T2 and/or the heat output enabling a precise control of the respective evaporated amount of liquid.

The essentially completely vaporized liquid escapes from the transport element. Due to for example capillary forces in the interior of the transport element, liquid is drawn from the liquid reservoir into the end of the transport element. Once the heating phase T2 is completed, the transport element can completely fill again in the resting phase T1. However, it is also conceivable that an incomplete filling of the transport element may be practical which is elucidated in more detail in the following. Subsequently the heating element is again activated so that a defined portion of liquid again evaporates. If the heating impulses are sent to the heating element in quick succession (short T1 times) there is not sufficient time to ensure the transport element is again completely filled. Consequently a new heating impulse can evaporate no more liquid than has flowed into the end of the transport element during the resting phase. Consequently a change in the resting phase T1 and hence of the period between two successive evaporation processes can influence the amount of evaporated liquid. In this case it is influenced by regulating the degree of filling of the end of the capillary when the time falls below the minimum for complete filling.

Hence the evaporation process can be directly influenced by controlling the heating phase and resting phases. The evaporation process is controlled such that it results in a liquid transport from the liquid reservoir into the transport element which is sufficiently continuous for the application and sets the desired flow rate. Consequently a desired flow rate is controlled by the length of the heating phase T2, the resting phase T1 and the heating capacity.

Hence a pulsed type of operation within the scope of the invention is characterized by the said parameters and by the fact that a combination of the said parameters corresponds to a particular amount of evaporated liquid and hence to a flow rate. In contrast to the prior art in which the heating element can also be in a resting or heating phase due to a temperature control mechanism, the resting and heating phase is not determined by an a-periodic temperature control mechanism as in the prior art but is used directly to control the flow rate.

The pulsed operation mode is advantageously achieved by activating the pump in less than 20% of the operating period.

In an advantageous embodiment at least one of the parameters (T1, T2, heating capacity) can be changed by the control unit of the micropump such that the flow rate can be adjusted by the control unit. The control unit can for example be in turn controlled by a program which for example specifies a cyclic flow rate time course that is adapted to an appropriate field of application. In this connection it is for example conceivable that the flow rate is slowed down in cycles in a predetermined time interval in order to take up the analyte into the fluid and is accelerated again. However, it is also conceivable that the user of the micropump programs the control unit himself or changes the corresponding parameters as required.

In comparison to a continuous operation of a heating element, the described relationships between T1, T2 and the heating capacity allow an exact control of the flow rate. For example a decrease in the flow rate does not have to be achieved by reducing the temperature of heating elements which often requires a complicated control loop to adjust a specified temperature but can be achieved by modulating one or more of the said parameters (T1, T2, heating capacity). Consequently a change in flow rate can be controlled directly and without delays caused by the control mechanism. Moreover the pulsed operation of the heating element prevents an excessive heating of the transport element since it is cooled during the resting phases T1. In an advantageous embodiment the resting phase T1 is selected such that the transport element is essentially cooled to its ambient temperature. This supports a precise control of the flow rate since a heating up of the end of the transport element in continuous operation for example leads to a higher uncontrolled basal evaporation rate.

In an advantageous embodiment the heating phase T2 is additionally subdivided into signal pulses to avoid excessive heating up of the transport element. In addition to a more precise quantity of generated heat, this also allows an energy-saving operation of the micropump which is particularly advantageous for battery operated pumps. In this case the interval between the pulses within the heating phase is selected to be so short that there is almost no filling of the end of the transport element by inflowing liquid without it being immediately evaporated. Within the scope of the invention the heating phase is characterized in comparison to the resting phase. A subsequent inflow only occurs during the resting phase to an extent that the end of the transport element is again filled with liquid.

Consequently the heating phase can be controlled by a single signal or, as described, by several consecutive pulsed signals. For the inventive micropump it is not important in which manner the heating is initiated. It has turned out that in addition to the methods described above, the amount of heat can be controlled by varying the lengths of the pulses and the intervals between pulses within the heating phase resulting in an improved control of the flow rate.

All possible combinations of essentially periodically alternating pulses that can be used to adjust a constant flow rate are in principle conceivable to control the heating and resting phases.

A pulsed operation of a micropump can be carried out with a low evaporation rate of the micropump system at ambient temperature to facilitate an exact control also of low flow rates. However, an operation with a higher evaporation rate is conceivable in which the pump, due to its evaporation rate in the resting phase, has an increased flow rate which is due to the evaporation of the liquid at the ambient temperature of the pump. The evaporation rate of the liquid of a pump which is essentially caused by the ambient temperature is referred to as the basal flow rate in the invention. This can then in turn be increased by a pulsed operation of the heating element. An example of a micropump with a high evaporation rate is described for example in the Patent Application EP 1 167 757. Such a pump has the advantage that it can be operated with a particularly low energy consumption since the provision of the basal flow rate does not require an additional energy source if the ambient temperature is sufficiently constant.

It has turned out that in principle a wide variety of materials, material combinations and pump designs are possible for an application of the pulsed operating mode of a micropump according to the invention and hence the application is not limited to a specific pump model with a heating element. The energy consumption of the micropump is also reduced by the pulsed operating mode compared to a continuous operation.

The invention enables a new principle for an evaporation-based micropump for low flow rates. Despite its simplicity the micropump according to the invention is very reliable and cheap to manufacture.

The dependency of the micropump according to the invention on external factors such as the ambient temperature or the air humidity is improved compared to the prior art and the external effects can be reduced in a preferred embodiment using a sorbent in a closed gas space over the channel from which the fluid evaporates.

As already mentioned above the signal length, heating capacity and/or the time interval between two signals can be changed by the control unit in an advantageous embodiment of a micropump. One or more of these variables can be changed. A discontinuous control of the heating element in which for example pulses and the intervals between them are varied during the heating phase by the control unit, allows the evaporated fluid to be subdivided into increments thus enabling a digitalized control of the flow rate by the control unit in a preferred embodiment. It is for example then controlled by electrical signals from the control unit. In a preferred embodiment the signals of the control unit are passed to a resistance heating as the heating element. However, any form of a heating element maybe used. Thus for example a suitable device which heats the liquid with the aid of electromagnetic radiation can serve as the heating element.

Fluidic transport elements in the sense of the invention are understood as all structures that enable a transport of liquid. In a preferred embodiment it can be a channel which is for example designed such that it causes at least a portion of the fluid to subsequently flow into the end of the channel by capillary forces. It is also possible to have several channels or other transport elements within a micropump. For example such transport elements can be formed from twisted or parallel single threads that form strands. Such an embodiment of the transport element proves to be particularly advantageous for high flow rates since a particularly effective evaporation of the liquid occurs. However, a membrane or microporous structure through which the liquid can evaporate are also conceivable as transport elements. In this connection the said transport elements can each be provided with a heating element or several heating elements. A heating element may also be used for several transport elements. In such an embodiment the amount of heat generated can be passed on by the liquid located in the transport element so that one heating element may prove to be sufficient for several transport elements.

The heating element or heating elements are positioned within the end area of the transport element in such a manner that the heating element or heating elements are located inside a channel end. It is, however, also possible for the heating elements to be located outside the end of the transport element but be directly adjacent to it. An embodiment is mentioned here as an example in which the heating element adjoins a channel end but is located outside the channel. If the transport element is formed from a membrane, it can for example consist of a channel filled with a porous material, but an embodiment with a membrane that is described for example in the Patent Application EP 1 167 757 is also conceivable. The transport element can preferably be fluidically connected to a second additional transport element in a sequential manner. The second transport element is preferably in turn connected to a second liquid reservoir so that the liquids from the first and the second liquid reservoir are mixed within the first transport element. This embodiment is particularly advantageous when the liquid to be transported contains substances that do not readily evaporate which may lead to a concentration and deposition of these substances at the end of the transport element. Hence a dilution of the liquid to be transported by means of a second liquid reservoir prevents the blockage of the transport element and ensures a constant transport of liquid over long time periods.

The essentially completely evaporated fluid can for example escape from the transport element in the vicinity of the micropump. However, it is advantageous to pass the evaporated liquid into a sorption area such that the vicinity or optionally the sorption area represents at least a part of the evaporation area of the pump.

The sorption area is then arranged outside the fluidic transport element and contains a sorbent. The sorbent can absorb the evaporated liquid such that the liquid is essentially completely captured by the sorbent and the vapour pressure in the evaporation area remains essentially constant. Apart from the vapour pressure of the evaporation area of the pump, the transport rate of the liquid, as already mentioned above, also depends on the temperature which in turn influences the viscosity of the liquid among others. The viscosity of the liquid and the surface tension decrease with increasing temperature. Conversely a temperature increase affects the evaporation rate. Consequently there is a complex relationship between the flow rate and temperature of the environment of the micropump which can lead to variations in the flow rate. This is particularly the case for pumps with a high basal flow rate since the basal flow rate is directly dependent on the properties of the environment. However, suitable selection of the sorbent can ensure that the dependence on the environmental conditions is small which essentially eliminates interference in the described preferred embodiment.

An example of a pump containing a sorbent in which the total amount of the liquid to be transported is, however, limited by the absorption capacity of the sorbent is described in the Patent Application EP 1 167 757. The pump design is based on a controlled transport of liquids through a membrane into a gas space in which a sorbent is located. Provided the sorbent in the chamber is able to maintain the vapour pressure below the saturation vapour pressure, liquid evaporates from the membrane into the chamber. Due to the evaporated liquid, liquid is continuously resupplied from a liquid reservoir by the capillary forces in the membrane. An inventive embodiment of a micropump in combination with an analogous arrangement of a sorption area reduces the dependence on the vapour pressure and improves the control of the flow rate.

The term "sorbent" is intended to refer to adsorbents as well as absorbents. Sorbents are for example silica gels, molecular sieves, aluminium oxides, cellulite, clays, activated carbon, sodium sulfate, phosphorous pentoxide etc.

In a another advantageous embodiment the ambient temperature of the micropump e.g. in a microdialysis or ultrafiltration system is kept substantially constant by close contact to the human body. In this connection a direct contact of the housing in which the pump is located with the body surface is advantageous since this can ensure an almost constant ambient temperature. Furthermore a constant temperature control of the environment can be advantageously supported by thermally isolating the side of the pump system that does not rest against the body. Hence a dependence of the flow rate on interfering influences of the environment is thus substantially reduced.

Another subject matter of the invention is a method for operating a micropump. A heating phase is initiated by sending a first signal which causes heat evolution within a fluidic transport element of a micropump in the end area of a transport element. A heating phase takes place for a defined period T2 depending on the transmitted signal. As a result of the generated amount of heat, at least a portion of the liquid which is located inside the transport element evaporates. The essentially completely evaporated liquid escapes from the transport element. After completion of the heating phase the end area of the transport element cools resulting in an inflow of at least a portion of the liquid into the end of the transport element. After a particular period T1 after sending the first signal, a second signal is sent which initiates a new heating phase. Liquid is again evaporated from the transport element. As a result of the repeated initiation of the heating and resting phase, as described, liquid flows on into the end of the transport element in such a manner that a certain flow rate is set.

Advantageous embodiments of the method are derived as already described. The invention also concerns a microdialysis and an ultrafiltration system comprising a pump as described in which the microdialysis or ultrafiltration system advantageously has a sensor to detect one or more analytes in the liquid that is located downstream of the microdialysis or ultrafiltration membrane. As already described, in the ultrafiltration system, body fluid is drawn through the membrane into a channel such that one or more analytes can be detected in the body fluid. In the case of microdialysis the perfusate can be used directly as the liquid to be evaporated which is passed through a microdialysis catheter in order to take up the analyte. Alternatively it is also possible to provide a plurality of liquids such as a Ringer's solution where a fluid coupling occurs. In this case an evaporation process is used for the ultrafiltration in order to generate a negative pressure in the channel which draws body fluid into an ultrafiltration catheter.

The present invention is further elucidated by the figures.

Figure 1:
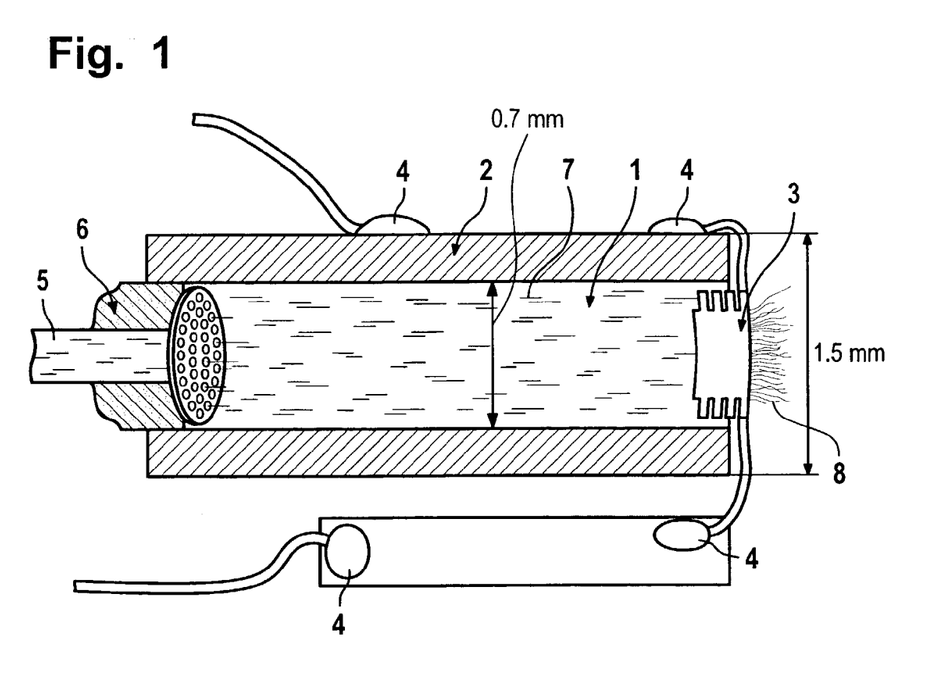
FIG. 1: micropump with heating element

FIG. 1 shows the construction of a micropump. The core of the pump is a steel strand (1) which is located in a brass jacket (2). The heating element (3) is formed by a coiled constantan wire which is located at the end of the strand (1). The resistance of the constantan wire is essentially indepen dent of temperature such that the following applies for the power (P) of the heating element:

$$P = \frac{U^2}{R}$$

in which U=voltage and R=resistance

The amount of heat generated (Q) is given by the approximation:

$$Q = P*t$$

in which t is the time period during which current flows through the resistor.

Hence the amount of heat generated can be defined by adjusting the applied voltage for a selected time period. The amount of heat generated (Q) is in turn directly proportional to the volume (V) of the evaporated fluid.

$$V = K*Q$$

In this case the proportionality constant (K) is determined by the fluid-specific quantity of heat that is necessary to evaporate the fluid starting with the temperature of the fluid in the resting phase.

The flow rate (V) is thus directly proportional to the heating capacity $$V = K*P$$

The steel strand (1) forms the fluidic transport element and has a cross-section of ca. 100 μm. The heating (3) is connected with electrical connectors (4). At the other end of the steel strand the fluid transport element is connected to a liquid reservoir (5) via a channel. The fluidic connection is sealed by a suitable adhesive e.g. an epoxide resin (6). The liquid to be transported (7) is located in the transport element (1). The liquid is evaporated by activating the heating element (3) by means of an electrical signal which is shown schematically in FIG. 1 by vapour (8). This results in a pumping action which sets a flow rate that depends on the amount of heat generated. The micropump shown can for example be used to achieve flow rates between 1 and 1000 nl/min.

Figure 2:
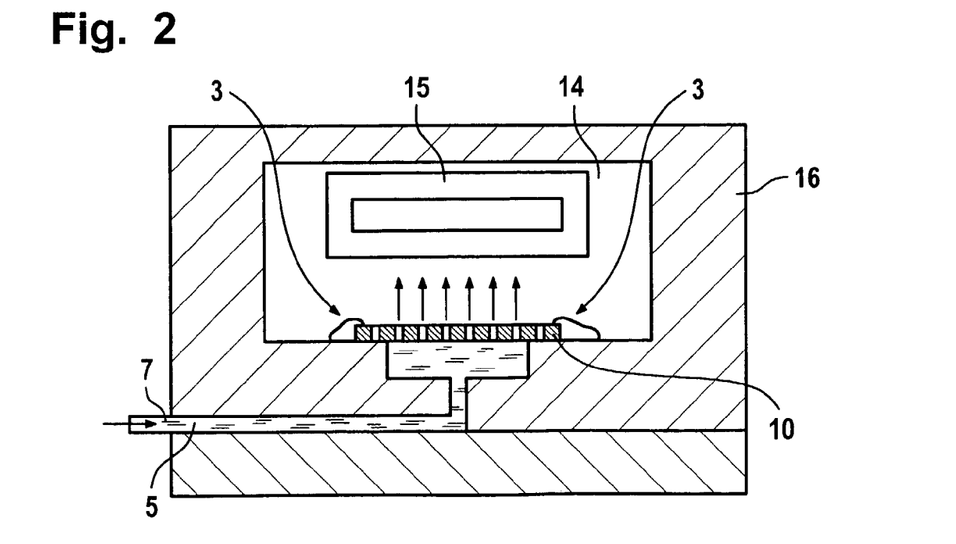
FIG. 2: micropump with a high basal evaporation rate and sorption area

FIG. 2 shows a micropump in which the fluidic transport element is formed by a membrane (10). The membrane (10) is connected to a fluid reservoir (5). Two heating elements (3) are positioned on the membrane (10). When the heating elements are activated, the heat generated on the heating elements is conducted within the membrane by means of the liquid to be transported (7). The liquid is evaporated uniformly from the membrane into a sorption area (14). A sorbent (15) is located in the sorption area which absorbs the evaporated liquid. The sorption area (14) is enclosed by the pump housing (16). The micropump arrangement that is shown ensures that the pump can operate essentially independently of the properties of the environment such as the air humidity. A pumping action without additional heating is also achieved due to the capillary effect of the membrane structure and of the sorbent which ensures a constant vapour pressure in the sorption area which results in a basal flow rate. Hence the arrangement shown enables a specific control of a flow rate which is larger than the basal flow rate of the micropump.

Figure 3A:
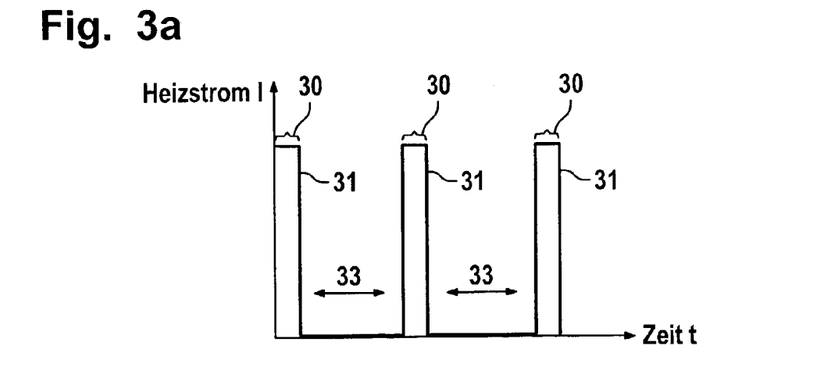
FIG. 3: pulse sequence during a heating and resting phase
Figure 3B:
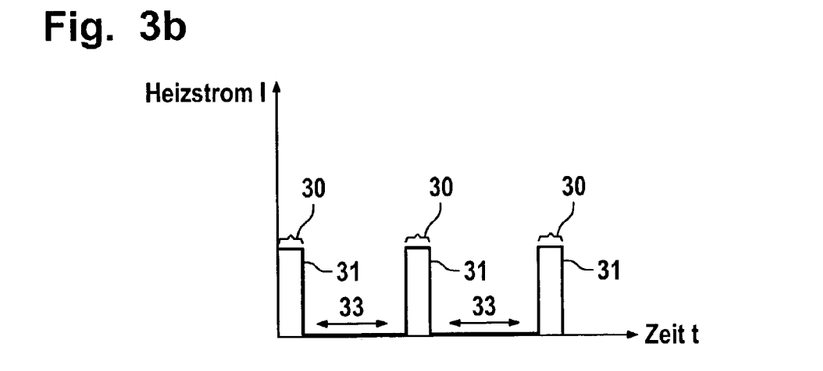

FIGS. 3a and 3b show an example of a sequence of three pulses (31) which are each generated during the heating phase T2 (30) by a current I. After the heating phase (30) the current flow is interrupted such that the heat output in the resting phase T1 (33) is zero. The heat output during the heating phase is constant in the example shown. FIG. 3a differs from FIG. 3b by a reduced heat output during the heating phase. The length of the heating and resting phases are identical in FIGS. 3a and 3b. A reduction of the heat output leads to a reduction of the amount of heat generated under the conditions shown which results in a reduced flow rate compared to FIG. 3a.

Figure 3C:
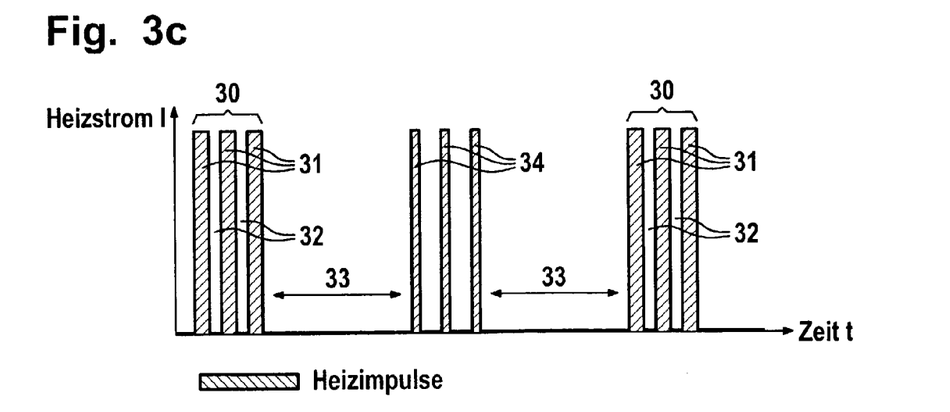

FIG. 3c shows an example of a sequence of pulses during a heating and resting phase in which the heating phase T2 (30) is divided into three pulses of equal length (31) with an identical output. The pulses (31) are separated by pulse pauses (32) of a duration T. The duration of the pulse pauses and of the pulses is identical. The resting phase T1 (33) begins after the last heat pulse. The resting phase is interrupted by a pulse combination of three short heating pulses (34) where the pulse pauses between the heating pulses (34) are considerably longer than the duration of the pulses. This is followed by another resting phase (33) and a heating phase (30).

The heating phase (30) results in a defined-build up of heat in the transport element. The amount of heat generated can be precisely controlled by selection of short consecutive pulses without excessively heating up the end of the transport element. The heat generation evaporates the liquid present in the transport element. The end of the transport element is not filled again during the heating phase. The end of the transport element is only filled again during the resting phase (33) during which liquid flows from a liquid reservoir into the end of the transport element. The heating pulses (34) serve to ensure a constant pump output without interruption of the flow rate during the resting phases. Moreover the heating pulses (34) prevent fluctuations in the flow rate which can occur if resting phases are selected which are too long. This is due to a certain inertness of the system since the evaporated liquid does not start to be replenished until some time after the end of a heating impulse. The insertion of a low power heating block as shown by the heating pulses (34) thus enables a constant flow rate with a minimal energy consumption. After a repeated resting phase (33) the heating phase (30) starts again.

The pulse sequences shown are intended to only represent an example of many possibilities. The described combination of pulses and other variants can easily be realized by appropriate electronics in the control unit of the micropump.

Figure 4A:
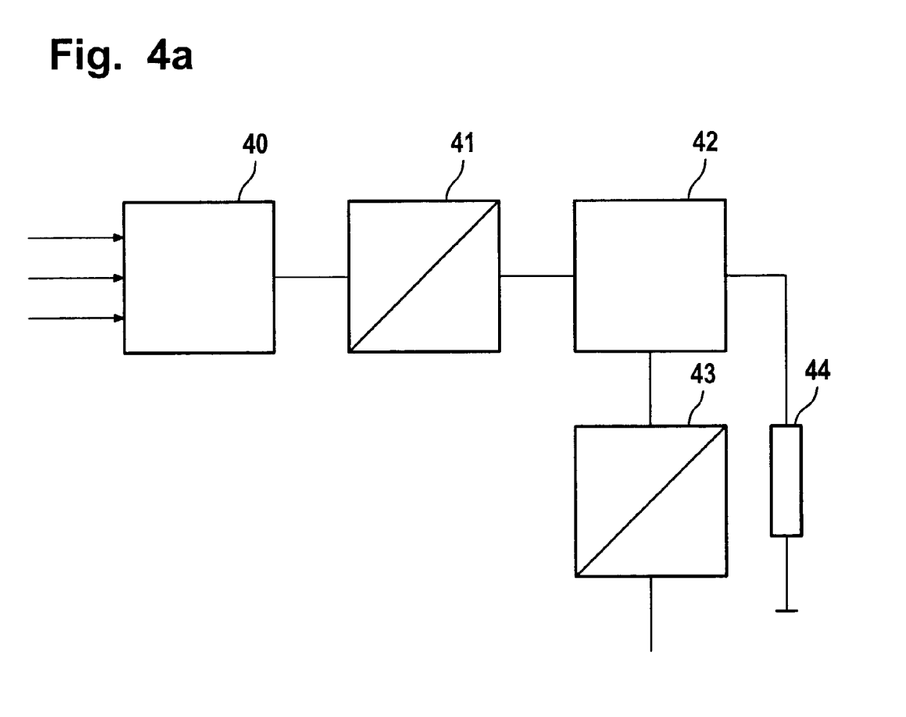
FIG. 4: circuit diagram of a pulse generator

FIG. 4 shows a simplified block diagram which can be used for example to control the heating. The pulse generator consists of a microprocessor (40) with a digital/analogue converter (41) that is connected via a power amplifier (42) to a heating element (44).

The pulse generator is supplied with current by means of a power unit (43). In order to generate a pulse sequence like that shown in FIG. 4b, the programmable microprocessor is programmed in a suitable programming language that is provided by the manufacturer. The individual programming steps are elucidated in more detail on the basis of the schematic sequence of pulses. In this connection the programming steps each occur with a pause without these being individually shown in the description.

Firstly a start command is given to run the program

The microprocessor then transmits a voltage value which corresponds to the power during the first pulse and the duration of the first pulse which defines a first pulse (31) like that of FIG. 3.

Subsequently a voltage value which corresponds to the power during the first pulse pause and the duration of the first pulse pause is determined and transmitted.

A recursion command is defined for the said steps in order to repeat the pulse n times.

These programming steps thus result in a first heating phase (30) as already illustrated in FIG. 3c.

Subsequently a voltage value is transmitted which corresponds to the power during a first long pause and the duration of a first long pause so that a resting phase (33) occurs.

A recursion command characterized by the above steps is defined in order to periodically repeat the heating and resting phase.

If it is not intended to operate the micropump further, a stop command is given to stop the program so that there is essentially no pumping action, or in the case of a micropump with a high evaporation rate (see FIG. 2) the corresponding basal flow rate is achieved again.

Figure 4B:
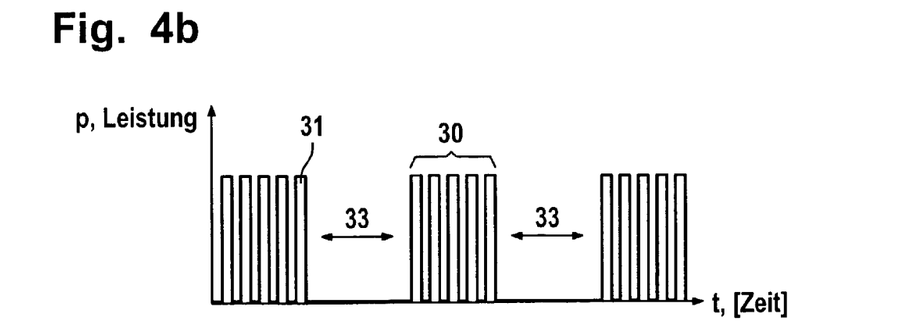

The digital data series generated according to the above instructions by the microprocessor is converted by the D/A converter into an analogue time/voltage curve. This time/voltage curve corresponds to the pulse sequence as shown in FIG. 4b.

The pulse sequence is amplified by the power amplifier which is supplied with power from the power unit and is passed as a heating current through the heating element.

The sequence of pulses shown is to be understood as an example. In principle more complex sequences of pulses can be programmed and generated by the method described above. It is also possible to regulate the flow rate by feedback from a measuring sensor which detects a temperature or a flow rate. In this connection the flow rate can for example be regulated by influencing the length of pulses or pauses or the power output: Such a regulation of the flow rate can then be effected by means of an a-periodic pulse sequence among others.

Figure 5A:
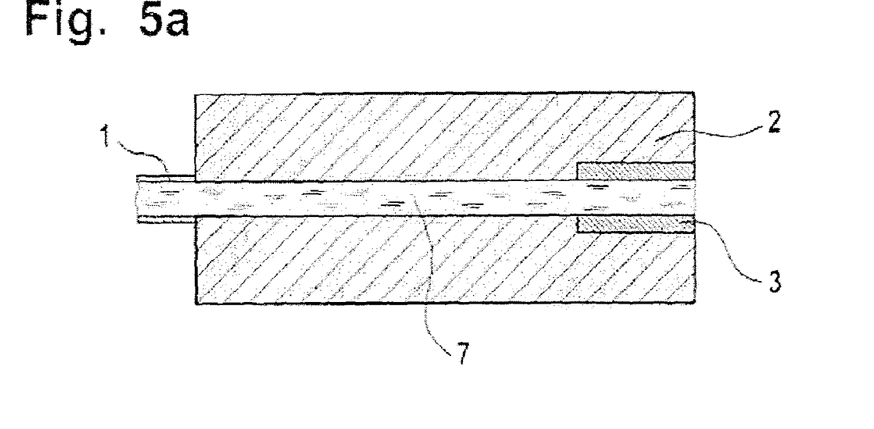
FIG. 5: schematic representation of a pump cycle
Figure 5B:
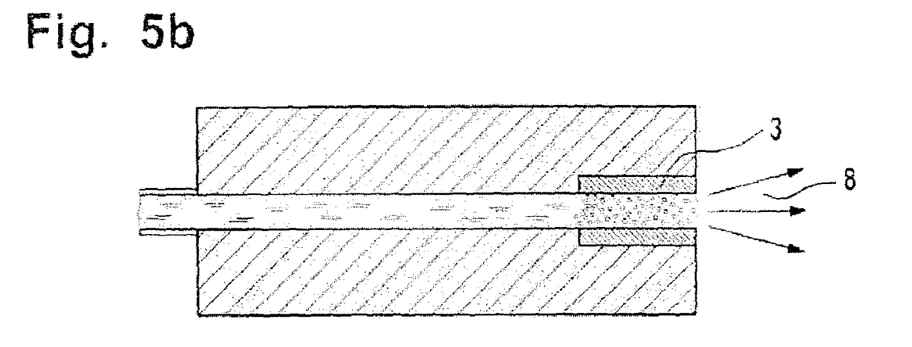
Figure 5C:
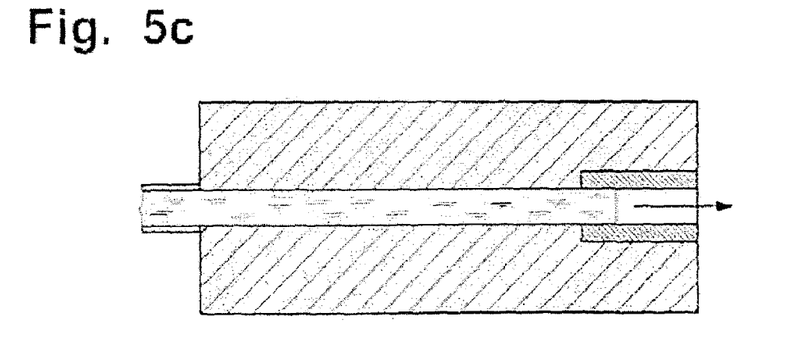

FIG. 5 also schematically illustrates the time course of a pump cycle. At the start of the pump cycle, the fluidic transport element (1) inside the pump body (2) is essentially completely filled with a liquid (7). A resistance heating is located at the end area of the transport element. If the heating is activated by a pulse, the heating is in a heating phase for a time period T2. During the heating phase T2 the liquid evaporates from the end area of the transport element. Once the vapour (8) has escaped from the transport element and the heating phase T2 has ended, liquid flows back into the end area of the transport element. The pump is now in a resting phase T1. During the resting phase T1 the end of the transport element is again filled with liquid such that a flow of liquid is formed within the pump. The inflowing liquid results in a pumping action which causes liquid transport within the system. The pump cycle is repeated by a new heating pulse according to FIGS. 5a to 5c.

The invention claimed is:

1. Micropump with a heating element comprising
a fluidic transport element which can be connected to a liquid reservoir and in the connected state makes a fluidic connection between the liquid reservoir and an evaporation area,
a heating element which is located in an end area of the transport element,
a control unit for controlling the healing element,
wherein the control unit controls the heating element by signals in such a manner that the heating element is alternately in a resting phase for a period T1 and in a heating phase for a period T2 and the resting phase and the heating phase alternate essentially periodically resulting in a pulsed operation of the heating element.

2. Micropump as claimed in claim 1
in which the flow rate of the micropump is determined by the length of the periods T1, T2 and by the heat output (HO) and at least one of the parameters (T1, T2, HO) can be changed by the control unit.

3. Micropump as claimed in claim 1,
in which the signal during the heating phase T2 is composed of several signals.

4. Micropump as claimed in claim 1,
in which the heating element is positioned inside the transport element.

5. Micropump as claimed in claim 1,
in which the heating element is positioned outside the transport element.

6. Micropump as claimed in claim 1,
in which the transport element is formed from individual threads which form strands.

7. Micropump as claimed in claim 1,
in which the signals of the control unit are electrical signals.

8. Micropump as claimed in claim 1,
in which the healing element is a resistance heater.

9. Micropump as claimed in claim 1,
in which at least two transport elements are present.

10. Micropump as claimed in claim 9,
in which the second transport element is fluidically connected to the first transport element and to a second liquid reservoir.

11. Micropump as claimed in claim 1,
in which at least two heating elements are present.

12. Micropump as claimed in claim 1,
in which to transport element is formed by a channel.

13. Micropump as claimed in claim 1,
in which the transport element is formed by a microporous structure.

14. Micropump as claimed in claim 1,
in which the transport elements and/or the heating elements are manufactured by microtechnical processes.

15. Micropump as claimed in claim 1,
which is connected to a liquid reservoir containing a liquid to be transported and the fluidic transport element is at least partially filled with the liquid to be transported.

16. Microdialysis system with a pump as claimed in claim 1, and a microdialysis catheter which has a microdialysis membrane across which the pump transports a liquid.

17. Microdialysis system as claimed in claim 16 with
a sensor located downstream of the microdialysis membrane for detecting one or more analytes in the liquid.

18. Ultrafiltration device having a pump as claimed in claim 1, and an ultrafiltration catheter which has an ultrafiltration membrane through which the body fluid can be drawn.

19. Ultrafiltration device as claimed in claim 18,
having a sensor located downstream of the ultrafiltration membrane for detecting one or more analytes in the body fluid.

* * * * *